United States Patent [19]

Brück

[11] 4,049,350

[45] Sept. 20, 1977

[54] PROCESS AND APPARATUS FOR DETECTING INCLUSIONS

[75] Inventor: Gernot Klaus Brück, Cologne, Germany

[73] Assignee: DIHACO Diamanten Handels Compagnie Est., Mauren, Fla.

[21] Appl. No.: 612,925

[22] Filed: Sept. 12, 1975

[30] Foreign Application Priority Data

Sept. 18, 1974 Germany ............................ 2444644

[51] Int. Cl.$^2$ ............................................ G01N 21/32
[52] U.S. Cl. ....................................... 356/30; 356/239
[58] Field of Search ................... 356/30, 31, 200, 239, 356/240

[56] References Cited

U.S. PATENT DOCUMENTS

| 3,586,444 | 6/1971 | Sproul et al. | 356/239 X |
| 3,609,380 | 9/1971 | Shaw, Jr. | 356/239 X |
| 3,867,032 | 2/1975 | Bruck | 356/30 |

Primary Examiner—F. L. Evans
Attorney, Agent, or Firm—Browdy and Neimark

[57] ABSTRACT

A process and apparatus for detecting inclusions in precious stones in which the stone is scanned with light from a laser. The stone is immersed in a liquid of the same refractive index as the stone so that there is no reflection from the outer surfaces of the stone, so that the shape of the stone does not affect the process.

26 Claims, 5 Drawing Figures

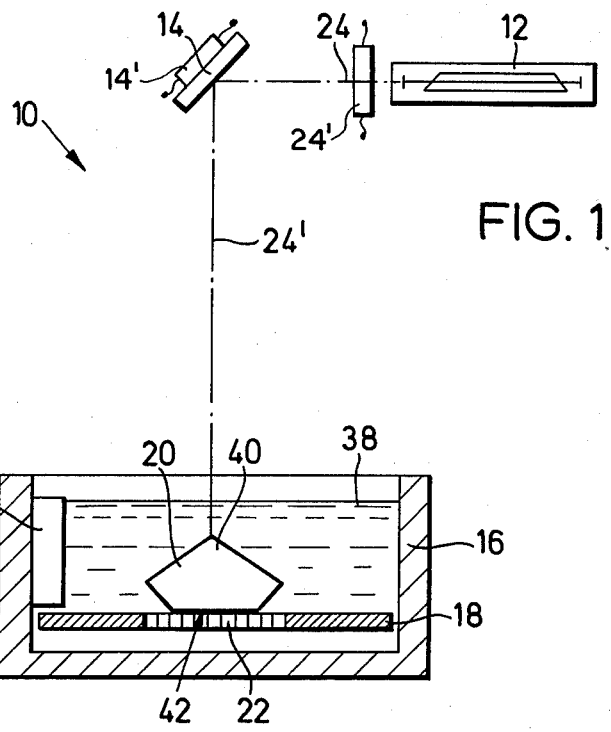
FIG. 1
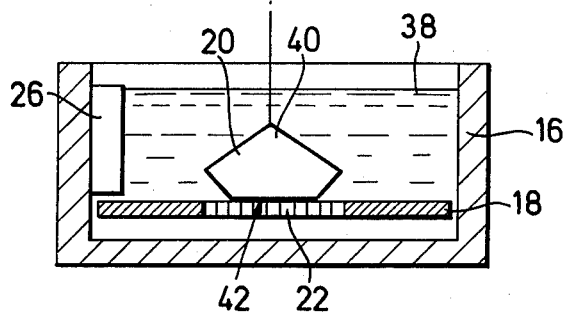
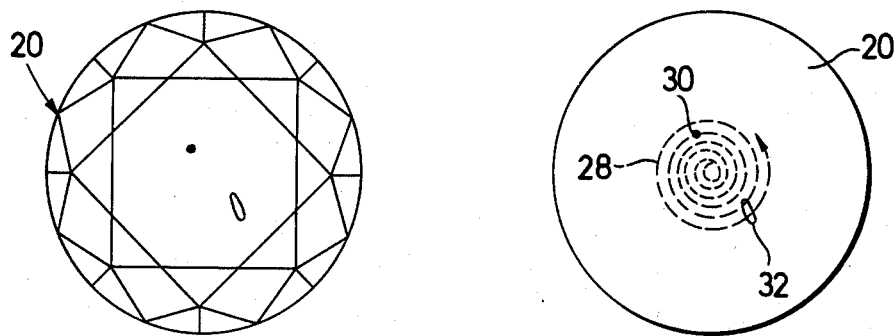
FIG. 2    FIG. 3
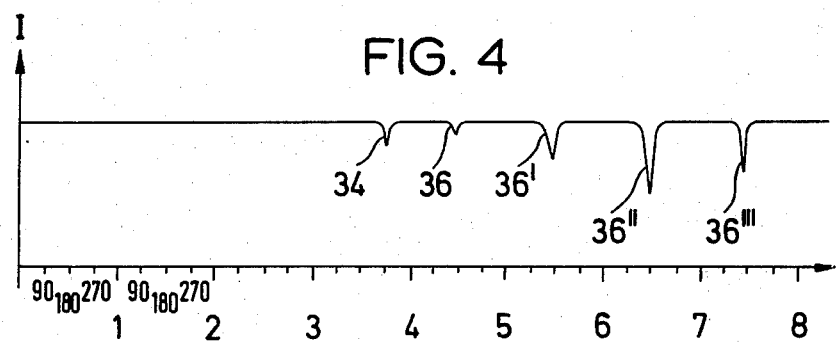
FIG. 4

PROCESS AND APPARATUS FOR DETECTING INCLUSIONS

BACKGROUND OF THE INVENTION

The invention relates to a process for detecting the presence of inclusions in, for example, precious stones and to an apparatus for the performance of the process.

The purity of the stones, that is, their freedom from inclusions, is usually ascertained by a technician with the naked eye, and in most cases with the use of a magnifying glass. It is obvious that the results of such an examination may vary, even if the rules for assessing the quality of a stone are scrupulously observed as the size of the inclusions often cannot be determined with the naked eye, even under a magnifying glass.

The object of the invention is to provide a process of the above kind, and an apparatus for its performance, enabling inclusions present in a precious stone to be detected objectively and independently of human impressions and preferably their size to be determined, preferably so that both the position and the size of the inclusions thus detected can be ascertained with the desired degree of accuracy. In this connection it should be borne in mind that the position of an inclusions in a precious stone may be likewise very important, as the value of the precious stone may be seriously reduced or else unaffected, according to the position of the inclusions and the extent to which it is apparent to the naked eye or noticeable in the over-all impression received of the precious stone.

SUMMARY OF THE INVENTION

The present invention provides a process for detecting inclusions in precious stones comprising scanning the stone with a concentrated beam of light, the cross-section of which is of the same order of magnitude as the smallest inclusions to be detected, the scanning taking place over its entire cross-sectional plane perpendicular to the incident beam and along scanning trajectories separated from one another by a distance not exceeding the beam cross-section, and measuring the intensity of the beam after it has been subjected to the influence of the stone.

In this process it is possible to utilize the total internal reflection angle and to introduce the beam into the stone at an angle which ensures that if the latter is flawless it will be totally internally reflected by the lower facet of the stone, e.g. the base. As soon as the beam encounters an inclusions it will be dispersed, so that for this part of the scanning of the beam total intense reflection does not take place. This part of the beam passes through the lower facet, the base, of the stone. It is possible to measure either the intensity of the totally reflected beam or the intensity of that part of the beam which passes through the base in the event of a dispersion to determine the presence of inclusions It is particularly preferable, however, for the stone under examination to be scanned while it is completely immersed in an immersion liquid and for the intensity of the beam passing through the stone to be measured continuously. The refraction index of the immersion liquid should preferably be as close as possible to the refractive index of the precious stone for the wave length of the incident beam, and in the examination of diamonds it is preferably between 2 and 2.4, particular preference being given to a refractive index of at least 2.2.

This process offers the following advantages. The apparatus for measuring the intensity of the beam influenced by the precious stone thus does not continuously, register background noise but registers the maximum singal, since in the case of a stone free of inclusions, the beam passes through the stone practically unimpeded since in the zone of the transition from the immersion liquid to the facets of the stone practically no refraction or reflection of the beam occurs, total reflection thus being prevented. If any inclusions are detected the resulting signals occur as so-called "breaks" in the continuously measured maximum signal. An optimum signal-to-noise ratio is thus obtained.

This latter method also obviates the difficulties which would arise without the use of the immersion liquid both in the zone of the central tip of a polished stone and in the marginal zones of the "rondist" plane and which could only be avoided by continuously adapting the incidence of the beam to the particular part of the stone under examination.

If, however, the precious stone to be examined has been completely immersed in a liquid with a high refractive index, so that the surface of the liquid is above the uppermost tip of the stone, and if the refractive index of the liquid is as close as possible to that of the stone itself, then the reflection problems accompanying the transition of the beam from the liquid to the stone are practically avoided. The beam can thus pass unimpeded through even the edge zones of the stone itself and reach the intensity measuring apparatus. Only if the beam encounters an inclusions will it be dispersed, the quantity of light passing through thus being greatly reduced.

The stone under examination is preferably scanned completely a second time in a different direction.

This offers the advantage that the exact spatial position of an inclusions detected in a stone by the first scanning operation can be calculated on the basis of the two scannings.

Furthermore, the stone under examination preferably undergoes at least one further scanning operation, at the same angle as before, after the immersion liquid has been agitated, for which purpose the immersion liquid is preferably irradiated, in between these scanning operations by an immersed ultrasonic transmitter, or is displaced by tilting the container if too viscous for the said irradiation.

In this step in the process it is possible by an appropriate comparison between the two measured results for interference effects due to solid particles in the immersion liquid or on the surface of the latter to be eliminated and for the signals which have been produced by solid particles remaining in a fixed position, such as inclusions in the stone, to be clearly obtained.

The cross-section selected for the light beam will preferably is about 0.03 mm and the distance between the scanning trajectories 0.02 mm.

This provides the advantage that even inclusions at the extreme limit of visibility for the naked eye can still be detected, the partial overlapping between the scanning trajectories making it doubly certain that no kind of occlusion will escape detection.

A laser beam is particularly preferred.

During scanning of the stone under examination, the incident beam and the stone can be relatively displaced, along a spiral trajectory. For preference, however, the incident beam and the stone being examined will be relatively displaced, so that the stone is scanned along parallel cross-sectional planes.

An apparatus in accordance with the invention, for detecting inclusions in precious stones comprises a container into which the stone to be examined is insertable with a predetermined alignment containing an immersion liquid of sufficient quantity to fully immerse the stone, a light source for producing a beam with a cross section of the same order of magnitude as the smallest inclusions to be detected, an adjusting device by which the beam can be aligned in a particular direction relative to the stone when inserted in the container and a moving device by which the stone and the beam are relatively moved, to scan the light beam across the stone.

The interior of the container is preferably fitted with an ultrasonic transmitter by which the immersion liquid is statistically agitated between the separate scanning operations.

The light source is preferably a laser apparatus, while the moving device preferably comprises at least one mirror by which the beam is reflected to the stone, the mirror itself being pivotable, to scan the beam across the stone.

To enable the mirror to be tilted, it can be mounted on a swivel shaft actuated by a driving device. It is also possible, in one advantageous embodiment of the invention to provide for the mirror tilting operation, an apparatus having electromechanical or piezoelectric elements which change their position or dimensions according to the electrical signals fed to them and which thus alter the position of the mirror.

In a further advantageous embodiment, the mirror comprises a rotating body, carrying a number of mirrors as facets, each at a certain preselected angle in respect of the longitudinal axis of the cylinder. In this case the angles of the mirrors can be all equal or else graduated. If the angles are all equal the rotating body has to fed forward by a preselected distance each time the beam of light has been tilted into position above the stone. If, on the other hand, the angles of the mirror are graduated, a number of planes of the stone can be scanned in succession on a complete revolution of the rotating body, which is then fed forward by a greater distance, i.e. by the sum of the separate distances of the planes scanned in the course of a rotation.

The moving device therefore, particularly comprises a feed device by which the mirror, after each pivoting operation, is displaced, perpendicularly to the scanning plane, by a preselected distance not exceeding the cross section of the beam, the feed device being preferably constructed on the lines of a micrometer screw.

In a particularly preferred embodiment of the invention, a photosensitive device which measures the intensity of the beam passing through the stone is provided on that side of the stone which faces away from the incident beam, e.g. in the zone of the floor of the container, preferably extending over a cross-sectional area at least equal to the maximum cross-sectional area of the stone.

BRIEF DESCRIPTION OF THE DRAWINGS

FIG. 1 is an apparatus for detecting the presence of inclusions in precious stones, and determining their size, with a light source consisting of a laser apparatus, the stone and the beam being relatively movable, along a spiral trajectory, FIG. 2 is a plan view of a polished precious stone with two inclusions, FIG. 3 is a schematic diagram of a spiral scanning trajectory, the two inclusions being situated within it, and FIG. 4 is a diagram of the signal emitted by the photosensitive device situated underneath the precious stone, the signal intensities being shown for the spiral trajectory, which are counted from the inside towards the outside and of which the angular position is indicated.

DESCRIPTION OF THE PREFERRED EMBODIMENT

Figure 5:
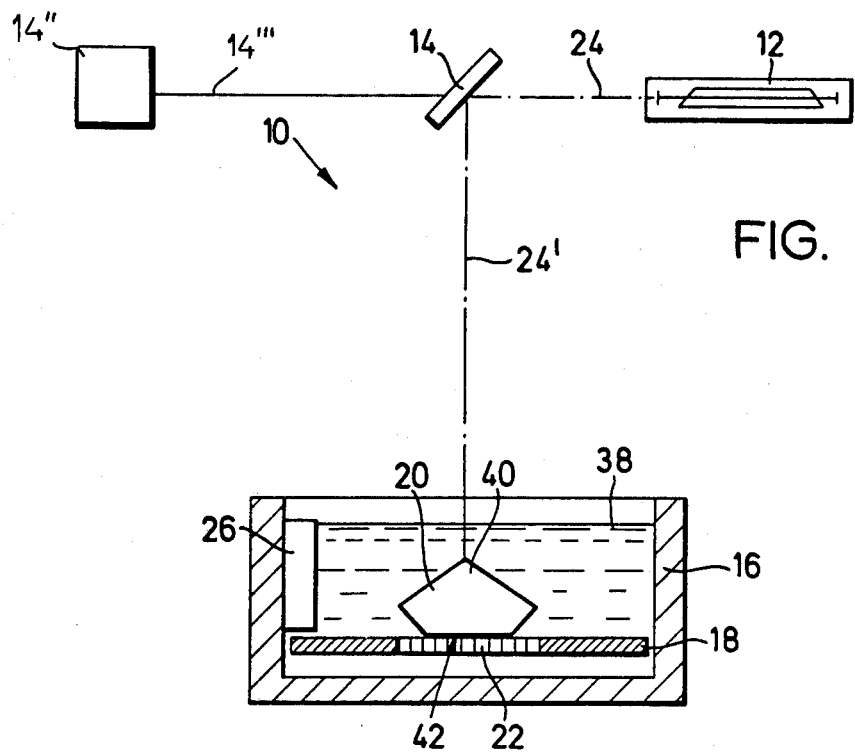
FIG. 5 is a schematic view of a second embodiment of the apparatus in accordance with the present invention.

As shown in the drawings, an apparatus 10 for detecting and measuring inclusions in precious stones comprises a laser 12, a mirror 14 and a container 16 of liquid having a refractive index generally equal to that of a stone to be tested, that is between 2 and 2.4 if the stone is a diamond. In the container 16 is a plate 18 which is parallel to its base and on which can be placed the precious stone 20 to be examined so that it is immersed in the liquid. A photo-sensitive device 22, comprising photo-conductive cells, photo-diodes or photo-conductive tubes, is inserted in the plate 18. The area over which the photo-sensitive device 22 extends in the plate 18 is such that even the largest stones to be examined can be accommodated by their projection surface on the plate 18 within this photosensitive device 22.

FIG. 1 shows a beam of light 24 whose cross-section is of the same order of magnitude as the smallest inclusion to be detected, i.e. 0.03 mm, which passes from the laser 12 to the mirror 14 and is reflected from the latter to the precious stone 20 so as to be normal to the base of the stone 20. An ultrasonic transmitter 26 is also provided on a side wall of the container 16 shown in FIG. 1.

It is possible, e.g. with a suitable means of driving the plate 18 in the container 16, this means being not shown in the drawing, and with a feed device 14, on the mirror 14, to rotate the stone 20 to be examined and at the same time to displace the laser ray 24 in the direction required to produce a spiral scanning trajectory to cover the entire stone, the successive spirals being closer than the cross-section of the beam, i.e. 0.02 mm. This means that the signal which is emitted by the photo-sensitive device 22 in the course of this movement and which directly depends on the intensity of the beam of light which has passed through the stone 20 constitutes a kind of spiral development of the volume of the stone 20 illustrated on a larger scale in FIG. 2, this process being indicated by the spiral line 28 in FIG. 3. A signal of this kind is shown in FIG. 4, in which the abscissa of the diagram gives the number of spiral turns, i.e. 1,2,3 etc., of the spiral line 28, proceeding from the inside towards the outside, these turns being subdivisible by angular degrees, while the ordinate gives the magnitude of the signal, i.e. the intensity of of particular beam of light which has passed through.

If a precious stone has two inclusions 30 and 32, as shown in FIG. 3, then the small inclusions 30, owing to its dispersion of the laser ray 24, will manifest itself as an interruption 34 to the maximum signal otherwise measured between the third and fourth spiral turn, at about 270°, while the large inclusions 32, in the zone of the spiral turns 3 to 8 and the subsequent turns will in each case occur shortly before 180° are reached, first increasing and then decreasing at 36, 36', 36'', 36''', likewise in the form of a break in the maximum signal otherwise continuously measured. Both the width and the multiple occurence of interruptions in the signal in succession to one another in the same angular position of successive spiral turns are an indication of the size of the inclusions detected.

A second scanning operation may be carried out from a different direction to determine the positions of the inclusions, between which the transmitter is operated to displace any dust on the surface or within the liquid.

Alternatively, or in addition, for the second scanning the container and stone may be tilted from the position of FIG. 1.

With the apparatus shown in FIG. 1 it is likewise possible to secure both the plate 18 and the container 16 in a permanent position, i.e., as shown in FIG. 5, it is likewise possible to secure the stone 20 in a permanent position and pivot the mirror 14 by means of a pivoting device 14 including electromechanical and/or piezo electric elements in such a way that the beam of light 24 is pivoted in planes perpendicular to the plane of the drawing, whilst at the same time a feed device 14 such as a micrometer screw is provided by which the mirror 14 as a whole is fed forward in small preselected steps, after each scanning operation, in the direction of that part of the beam of light 24 which extends from the laser 12 to the mirror 14.

The beam may also be tilted by electro-optical liquid crystal cells 24.

The mirror may be a rotating body carrying a number of mirrors as facets, each at a certain preselected angle in respect of the longitudinal axis of the rotating body. The angles of the mirrors may be graduated to provide separate scan lines.

I claim:

1. A process for detecting the presence and size of inclusions which scatter light in precious stones, comprising:
    scanning the stone, while the stone is submersed below the surface of an immersion fluid having a refractive index substantially equal to the refractive index of the stone for the wavelength of the incident beam, with a concentrated beam of light, the cross-section of which is of the same order of magnitude as the smallest inclusions to be detected and which scatter light from said beam, the scanning taking place over the entire cross-sectional plane of the stone perpendicular to the incident beam and along scanning trajectories separated from one another by a distance not exceeding the beam cross-section; and
    measuring, with respect to each position of said concentrated beam of light during said scanning step, the intensity of unscattered light of the beam after it has been subjected to the influence of the stone to the exclusion of light scattered by inclusions.

2. A process as claimed in claim 1, in which the refractive index of the immersion liquid is between 2 and 2.4 and the stone is diamond.

3. A process as claimed in claim 2, in which the refractive index of the immersion liquid is at least 2.2.

4. A process as claimed in claim 1 in which the stone under examination is aligned in such a way that the base thereof is situated at right angles to the axis of the beam and faces away from the incident beam of light.

5. A process as claimed in claim 1 in which the stone under examination is completely scanned a second time from a different direction.

6. A process as claimed in claim 1 further including scanning the stone at least one further time, in the same direction as before, after particles of the immersion liquid have been displaced.

7. A process as claimed in claim 6, in which the immersion liquid is irradiated before the further scanning operation with an immersed-ultrasonic transmitter.

8. A process as claimed in claim 6 in which the immersion liquid is displaced by tilting the container before the further scanning operation.

9. A process as claimed in claim 1 in which the cross-section of the beam of light is approximately 0.03 mm, and the distance between successive scanning trajectories is approximately 0.02 mm.

10. A process as claimed in claim 9 in which the beam of light is a laser beam.

11. A process as claimed in claim 1 in which the incident beam of light and the stone being examined are displaced in relation to each other, during the scanning of the stone, along a spiral trajectory.

12. A process as claimed in claim 1, in which the incident beam of light and the stone being examined are displaced in relation to each other, during scanning of the stone, so that the stone is scanned along parallel cross-sectional planes.

13. Apparatus for detecting the presence and size of inclusions which scatter light in stones, comprising:
    a container into which the stone to be examined in insertable with a predetermined alignment;
    an immersion liquid having a refractive index substantially equal to the refractive index of the stone for the wavelength of the incident beam, contained within the container in sufficient quantity to fully immerse the stone;
    a light source for producing a light beam with a cross-section of the same order of magnitude as the smallest inclusions to be detected and which scatter light from said beam;
    an adjusting device for aligning the beam in a particular direction relative to the stone when inserted in the container;
    a moving device for relatively moving the stone and the beam to scan the light beam across the stone; and
    means responsive to the intensity of unscattered light from said light beam to the exclusion of light scattered by inclusions for measuring the intensity of said unscattered light with respect to each relative position of the beam and the stone during the scan caused by said moving device.

14. Apparatus as claimed in claim 13, further including an ultrasonic transmitter mounted within said container for agitating the immersion liquid between separate scanning operations.

15. Apparatus as claimed in claim 13 in which the source of light consists of a laser apparatus.

16. Apparatus as claimed in claim 13 in which the moving device comprises at least one mirror by which the beam is reflected to the stone.

17. Apparatus as claimed in claim 16, in which the mirror is pivotable, to scan the beam across the stone along preselected planes.

18. Apparatus as claimed in claim 17, in which a device having electromechanical and piezo-electric elements is provided to enable the mirror to be tilted.

19. Apparatus as claimed in claim 13 in which said moving device includes a mirror comprising a rotating body carrying a number of mirrors as facets, each at a preselected angle in respect of the longitudinal axis of the rotating body.

20. Apparatus as claimed in claim 19, in which the angles of the mirrors are all equal.

21. Apparatus as claimed in claim 19, in which the angles of the mirrors are graduated to provide separate scan lines.

22. Apparatus as claimed in claim 17, in which the moving device comprises a feed device by which the mirror, after each pivoting operation, is displaced, perpendicularly to the scanning plane, by a preselected distance not exceeding the cross-section of the beam of light.

23. Apparatus as claimed in claim 22, in which the feed device includes a micrometer screw.

24. Apparatus as claimed in claim 13 in which the beam is tilted electro-optically by means of liquid crystal cells.

25. Apparatus as claimed in claim 13 in which a photo-sensitive device which measures the intensity of the beam passing through the stone is provided on that side of the said stone which faces away from the incident beam.

26. Apparatus as claimed in claim 25, in which the photo-sensitive device extends over an area at least equal to the area of the maximum cross-sectional plane of the stone.

* * * * *